United States Patent
Wang et al.

(10) Patent No.: US 10,792,123 B2
(45) Date of Patent: Oct. 6, 2020

(54) MASSAGE GUIDING DEVICE AND MASSAGE GUIDING METHOD

(71) Applicant: BOE TECHNOLOGY GROUP CO., LTD., Beijing (CN)

(72) Inventors: Xinan Wang, Beijing (CN); Jiantao Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1226 days.

(21) Appl. No.: 15/025,964

(22) PCT Filed: Oct. 30, 2015

(86) PCT No.: PCT/CN2015/093392
§ 371 (c)(1),
(2) Date: Mar. 30, 2016

(87) PCT Pub. No.: WO2016/192294
PCT Pub. Date: Dec. 8, 2016

(65) Prior Publication Data
US 2017/0128151 A1    May 11, 2017

(30) Foreign Application Priority Data
Jun. 2, 2015    (CN) .......................... 2015 1 0295787

(51) Int. Cl.
*A61H 99/00*    (2006.01)
*A61H 37/00*    (2006.01)
(Continued)

(52) U.S. Cl.
CPC ........... *A61B 90/361* (2016.02); *A61H 37/00* (2013.01); *A61H 39/02* (2013.01); *A61H 99/00* (2013.01);
(Continued)

(58) Field of Classification Search
CPC ........ A61H 99/00; A61H 37/00; A61H 39/02; A61H 2201/5097; A61H 2201/5092;
(Continued)

(56) References Cited

U.S. PATENT DOCUMENTS

| | | | | |
|---|---|---|---|---|
| 2004/0097851 A1* | 5/2004 | Inada | ................. | A61H 23/0254 601/47 |
| 2006/0031081 A1* | 2/2006 | Arne | ..................... | G06Q 30/02 705/1.1 |

(Continued)

FOREIGN PATENT DOCUMENTS

| CN | 101340880 A | 1/2009 |
|---|---|---|
| CN | 102622916 A * | 8/2012 |

(Continued)

OTHER PUBLICATIONS

International Search Report of PCT/CN2015/093392 in Chinese, dated Jan. 18, 2016 with English translation.
(Continued)

Primary Examiner — Boniface N Nganga
(74) Attorney, Agent, or Firm — Collard & Roe, P.C.

(57) ABSTRACT

A massage guiding device and a massage guiding method are provided. The massage guiding device includes: a main body (1); and an image recognition unit (2) and a projection unit (3) which are disposed on the main body (1). The image recognition unit (2) is configured to obtain an image of a person being massaged and determine massage information based on the image of the person being massaged. The projection unit (3) is configured to emit visible light according to the massage information as determined by the image recognition unit (2) so as to display the massage information on a body of the person being massaged. The massage guiding device is applicable in a massage process to solve the problems that unprofessional massagers cannot achieve
(Continued)

desired massage effect due to lacking of massage information or due to incorrect massage information.

8 Claims, 4 Drawing Sheets

(51) Int. Cl.
*A61H 39/02* (2006.01)
*A61B 90/00* (2016.01)

(52) U.S. Cl.
CPC ............... *A61H 2201/0188* (2013.01); *A61H 2201/5043* (2013.01); *A61H 2201/5048* (2013.01); *A61H 2201/5092* (2013.01); *A61H 2201/5097* (2013.01)

(58) Field of Classification Search
CPC .... A61H 2201/5048; A61H 2201/5043; A61H 2201/0188; A61B 90/361
See application file for complete search history.

(56) References Cited

U.S. PATENT DOCUMENTS

| | | | | |
|---|---|---|---|---|
| 2008/0312718 | A1* | 12/2008 | Kulkarni | A61H 39/02 |
| | | | | 607/59 |
| 2009/0288017 | A1* | 11/2009 | Just | A61G 13/10 |
| | | | | 715/750 |
| 2011/0176119 | A1* | 7/2011 | Jung | H04N 9/3179 |
| | | | | 353/79 |
| 2014/0223462 | A1* | 8/2014 | Aimone | A61B 5/0476 |
| | | | | 725/10 |
| 2016/0058644 | A1* | 3/2016 | Cheatham, III | A61H 1/008 |
| | | | | 601/84 |

FOREIGN PATENT DOCUMENTS

| | | |
|---|---|---|
| CN | 102622916 A | 8/2012 |
| CN | 102698370 A | 10/2012 |
| CN | 103077649 A | 5/2013 |
| CN | 103285510 A | 9/2013 |
| CN | 103735407 A | 4/2014 |
| CN | 104873381 A | 9/2015 |
| KR | 10-2009-0020051 A | 2/2009 |
| WO | 2006/030462 A1 | 3/2006 |
| WO | 2010/150018 A1 | 12/2010 |

OTHER PUBLICATIONS

Notice of Transmittal of the International Search Report of PCT/CN2015/093392 in Chinese, dated Jan. 18, 2016.
Written Opinion of the International Searching Authority of PCT/CN2015/093392 in Chinese, dated Jan. 18, 2016 with English translation.
Chinese Office Action in Chinese Application No. 201510295787.3, dated Aug. 30, 2016 with English translation.
Second Chinese Office Action in Chinese Application No. 201510295787.3, dated Apr. 19, 2017 with English translation.

* cited by examiner

MASSAGE GUIDING DEVICE AND MASSAGE GUIDING METHOD

CROSS REFERENCE TO RELATED APPLICATIONS

This application is the National Stage of PCT/CN2015/093392 filed on Oct. 30, 2015, which claims priority under 35 U.S.C. § 119 of Chinese Application No. 201510295787.3 filed on Jun. 2, 2015, the disclosure of which is incorporated by reference.

FIELD

At least one embodiment of the present invention relates to a massage guiding device and a massage guiding method.

BACKGROUND

In daily life, more and more people have begun to pay their attention on body healthy. Usually, people choose to ease fatigue by means of massage performed by themselves or friends and families. During massage, people normally act arbitrarily, that is, to massage portions of the body which are feeling tired. However, the applicant of the present application have discovered that, during such arbitrary massage, unprofessional massagers are very likely to act on incorrect portions of the body or act with excessively larger massage strength, that is, massage information such as massage location or massage strength may be not accurate enough, which may lead to difficulty in achieving desired massage effect or may lead to unintentional injury.

SUMMARY

On one aspect, embodiments of the present invention provide a massage guiding device, comprising: a main body; and an image recognition unit and a projection unit which are disposed on the main body.

The image recognition unit is configured to obtain an image of a person being massaged and determine massage information based on the image of the person being massaged as obtained.

The projection unit is configured to emit visible light according to the massage information so as to display the massage information on a body of the person being massaged.

On the other aspect, embodiments of the present invention further provide a massage guiding method, comprising: obtaining an image of a person being massaged; determining massage information based on the image of the person being massaged as obtained; and emitting visible light according to the massage information so as to display the massage information on a body of the person being massaged.

BRIEF DESCRIPTION OF THE DRAWINGS

In order to clearly illustrate the technical solution of the embodiments of the present invention, the drawings of the embodiments will be briefly described in the following, wherein.

NUMERAL REFERENCES

1-main body; 2-image recognition unit; 3-projection unit; 4-setting unit; 5-storage unit; 6-control unit; 7-sounding unit; 8-physiotherapy unit; 9-mounting unit; 10-remote control unit; 11-wearable unit.

DETAILED DESCRIPTION

In order to make objects, technical solutions and advantages of the embodiments of the present invention apparent, the technical solutions of the embodiment will be described in a clearly and fully understandable way in connection with the drawings related to the embodiments of the present invention. It is obvious that the described embodiments are just a part but not all of the embodiments of the present invention. Based on the described embodiments herein, those skilled in the art can obtain other embodiment(s), without any inventive work, which should be within the scope of the present invention.

Unless otherwise defined, all the technical and scientific terms used herein have the same meanings as commonly understood by one of ordinary skill in the art to which the present invention belongs. The terms, such as "first," "second," or the like, which are used in the description and the claims of the present application, are not intended to indicate any sequence, amount or importance, but for distinguishing various components. Also, the terms, such as "a/an," "one," or the like, are not intended to limit the amount, but for indicating the existence of at lease one. The terms, such as "comprise/comprising," "include/including," or the like are intended to specify that the elements or the objects stated before these terms encompass the elements or the objects and equivalents thereof listed after these terms, but not preclude other elements or objects. The terms, "on," "under," or the like are only used to indicate relative position relationship, and when the position of the object which is described is changed, the relative position relationship may be changed accordingly.

Hereafter, particular embodiments of the present invention are further described in more details, in which certain features and structures are omitted for clarity of explanation; however, the way of description is not intended to limit the embodiments of the invention to comprise only the features and structures as described herein but also other necessary ones.

The First Embodiment

Figure 1:
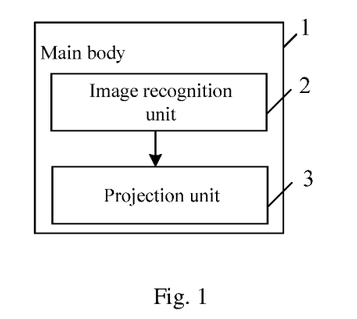
FIG. 1 is a schematic diagram illustrating a massage guiding device as provided by an embodiment of the present invention.

An embodiment of the present invention provides a massage guiding device. As illustrated in FIG. 1, the massage guiding device comprises a main body 1; and an image recognition unit 2 and a projection unit 3 which are disposed on the main body 1; the image recognition unit 2 is configured to obtain an image of a person being massaged and determine massage information as required by the person being massaged based on the image of the person being massaged; the projection unit 3 is configured to emit visible light according to the massage information determined by the image recognition unit 2 so as to display the massage information on a body of the person being massaged.

Figure 2:
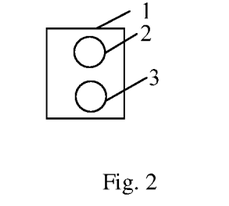
FIG. 2 is a schematic diagram illustrating a main body of a massage guiding device as provided by an embodiment of the present invention.

It should be explained that, first of all, neither a shape nor a structure of the main body 1 is particularly defined in embodiments of the present invention; By way of example, as illustrated in FIG. 2, the main body 1 can be a solid structure provided with the image recognition unit 2 and the projection unit 3; in addition, neither a shape nor a structure of the image recognition unit 2 or the projection unit 3 is particularly defined in embodiments of the present invention, either; Secondly, the image of the person being massaged can comprise profile information of the person being massaged, posture information of the person being massaged and the like, wherein the profile information of the person being massaged can comprise information on a stature or weight status (fat or skinny) of the person being massaged, while the posture information of the person being massaged can comprise one of sitting posture, lying posture and standing posture; wherein the lying posture can comprise lying prostrate, lying supine and lying on side; as a result, it's possible to determine the massage information based on the profile information of the person being massaged or the posture information of the person being massaged; Thirdly, the massage information can comprise at least one of massage location, massage sequence, massage direction, massage strength, massage duration and massage manipulation, wherein the massage location refers to an acupuncture point to be massaged or a local area to be massaged; the massage sequence refers to a sequence through which the massage is performed from one massage location to a next massage location; the massage direction refers to a direction along which the massage is performed continuously from one massage location to another massage location; the massage duration refers to a period of time for the massage to be performed at a same massage location; the massage manipulation comprises pressing, pushing, rubbing, knocking, pinching and the like.

By way of example, the image of the person being massaged comprises the profile information of the person being massaged. During usage of the massage guiding device, the image recognition unit 2 obtains the image of the person being massaged by taking or scanning a picture of the person being massaged, and then matches the image of the person being massaged with the profile information stored in the massage guiding device to determine the massage information; the projection unit 3 then displays the massage information on a body of the person being massaged according to the massage information. By way of example, the projection unit 3 displays the massage location in a form of light spot on the body of the person being massaged; displays the massage sequence by moving the light spot in saltatory motion; displays the massage direction by moving the light spot in continuous motion, that is, displays a massage manner in which the massage is continuously performed from one massage location to another massage location; displays the massage strength by allowing the number of light circle around the light spot being in direct proportion to the massage strength; displays the massage duration by means of numbers, for example, displays a massage duration of 1 minute by projecting a number "1" and displays a massage duration of half a minute by projecting a number "0.5"; or displays the massage duration by moving the light spot, that is, moving the light spot to the next massage location upon the current massage duration is ended; displays the massage manipulation by displaying signs on the body of the person being massaged, for example, displays "pressing" by displaying a sign of palm, displays "knocking" by displaying a sign of fist, and displays a faster knocking by displaying a sign of "+" while displays a slower knocking by displaying a sign of "−". It should be explained that, the above is merely described by way of example, and the massage information can be represented by other figures, colors and the like, because a projection device is capable of displaying plentiful image information such as arbitrary shape, brightness and color.

In addition, by way of example, the image of person being massaged comprises the posture information of the person being massaged. During usage of the massage guiding device, the image recognition unit 2 obtains the image of the person being massaged by taking or scanning a picture of the person being massaged, and matches the image of person being massaged as obtained with the posture information stored in the massage guiding device so as to determine a posture of the person being massaged; the image recognition unit 2 then determines the massage information based on the posture of the person being massaged; the projection unit 3 then displays the massage information on the body of the person being massaged according to the massage information.

With the massage guiding device as provided by embodiments of the present invention, the image recognition unit 2 can determine massage information based on the image of the person being massaged as obtained and then the projection unit 3 can display massage information on the body of the person being massaged according to the above-mentioned massage information; consequently, as compared with existing technology in which the massage information is not correct enough, embodiments of the present invention allow to accurately massage the person being massaged according to the massage information displayed on the body of the person being massaged without occurrence of incorrect massage location or improper massage strength, so as to achieve desired massage effect. Moreover, the massage is performed by following the massage information, thus it can avoid any injury to the body of the person being massaged.

Either of the following two illustrative structures can be applied in the above-mentioned embodiments to satisfy the demands of the person being massaged.

Figure 3:
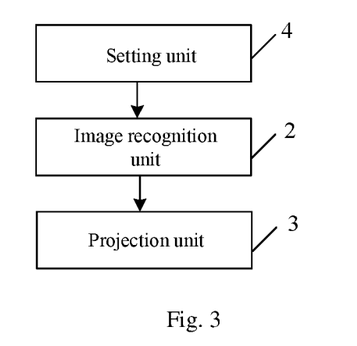
FIG. 3 is another schematic diagram illustrating a massage guiding device as provided by an embodiment of the present invention.

One of the example structures is illustrated in FIG. 3 where a setting unit 4 is further disposed on the main body 1 and is connected to the image recognition unit 2; the setting unit 4 is configured to detect basic information of the person being massaged as input by a user; in such case, the image recognition unit 2 is further configured to obtain the basic information as detected by the setting unit 4 and determine the massage information based on the image of person being massaged and the basic information of the person being massaged.

It should be explained that, first of all, a user can be any relevant person such as a person being massaged and a massager; secondly, the basic information can comprise at least one of sex, age, stature, weight, desired massage strength and desired massage mode, wherein the massage mode comprises local massage and full-body massage, and the local massage comprises head massage, shoulder massage, upper body massage, abdominal massage, limbs massage and foot massage.

During usage, the setting unit 4 detects the basic information of the person being massaged as input by the user through touch detection technology or key detection technology; the image recognition unit 2 obtains the image of the person being massaged and the basic information as detected by the setting unit 4, and determines the massage information according to the image and the basic information of the person being massaged. By way of example, given that the setting unit 4 is provided with a touch unit to detect the massage mode of the person being massaged as a full-body massage and given that the image recognition unit 2 recognizes the posture of the person being massaged as lying supine, the image recognition unit 2 then displays information such as massage location and massage strength on the whole body of the person being massaged according to the posture of lying supine as recognized by itself and the massage mode of full-body massage as set by the setting unit 4. It can satisfy various demands from different types of people being massaged because the massage information can be determined based on the basic information of the person being massaged.

Figure 4:
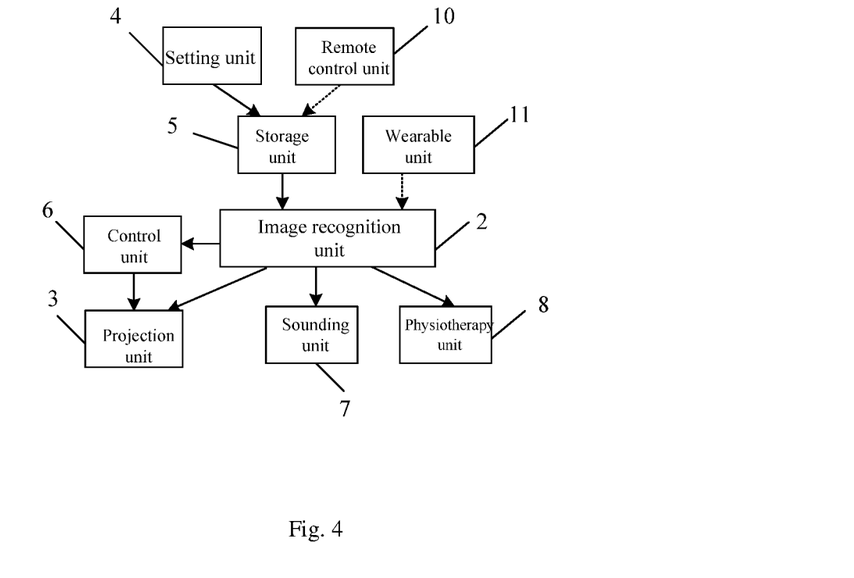
FIG. 4 is yet another schematic diagram illustrating a massage guiding device as provided by an embodiment of the present invention.

The other one of the illustrative structures is illustrated in FIG. 4. In order to eliminate the need of repeatedly inputting the basic information of the person being massaged by the user, the main body 1 is provided with a setting unit 4 and a storage unit 5 which is connected to the setting unit 4 and to the image recognition unit 2 respectively; the setting unit 4 is configured to detect the basic information of the person being massaged as input by the user; the storage unit 5 is configured to obtain the basic information as detected by the setting unit 4 and store the same; in such case, the image recognition unit 2 is further configured to obtain the basic information as stored by the storage unit 5 and determine the massage information according to the basic information as stored in the storage unit 5; as a result, the user can invoke the basic information as stored in the storage unit 5 upon a first input without repeatedly inputting the basic information of the person being massaged.

It should be explained that, the storage unit 5 can store basic information of a plurality of people being massaged. In case that the storage unit 5 stores basic information of a plurality of people being massaged, the image recognition unit 2 can identify the person being massaged according to the profile information in the image of the person being massaged in combination with the basic information of the person being massaged such as stature and weight, so as to determine the massage strength and the massage mode as required by the person being massaged; it's also possible that, for example, the setting unit 4 detects the person being massaged as chosen by the user, the storage unit 5 then invokes the basic information of the corresponding person being massaged, and the image recognition unit 2 then determines the massage information according to the image and the basic information of the person being massaged.

In the above-mentioned embodiments, as illustrated in FIG. 4, in order to allow the visible light as emitted from the projection unit 3 to have variable orientation and variable light quantity, for example, the main body 1 can be further provided with a control unit 6 connected to the image recognition unit 2 and the projection unit 3 respectively; the control unit 6 is configured to control a rotation of a light output of the projection unit 3 and a f-number of the light output according to the massage information as determined by the image recognition unit 2. By controlling the rotation of the light output of the projection unit 3 and the f-number of the light output, it can change the orientation of the visible light as emitted from the projection unit 3 so as to change the direction of the massage location as displayed by the projection unit 3. By way of example, in case that the user switches the massage mode, e.g., from a head massage to a limbs massage, the control unit 6 changes from controlling the projection unit 3 to display the massage information on the head of the person being massaged to controlling the projection unit 3 to display the massage information on the limbs of the person being massaged. For another example, under some circumstances where the massage guiding device is required to display massage information on bodies of different people being massaged, the control unit 6 can control the rotation of the projection unit 3 to be adapted to people being massaged with different statures; moreover, a luminous flux of the visible light as emitted from the projection unit 3 can be changed by controlling the f-number of the light output of the projection unit 3; by way of example, it can increase the luminous flux for the person being massaged who is relatively taller so that the projection unit 3 can display the massage information clearly on portions of the body of the patient far away from the massage guiding device.

In the above-mentioned embodiments, as illustrated in FIG. 4, in order to provide the user with massage information more clearly, for example, the main body 4 can be further provided with a sounding unit 7 connected to the image recognition unit 2; the sounding unit 7 is configured to produce a sound according to the massage information as determined by the image recognition unit 2 at the same time when the projection unit 3 displays the massage information on the body of the person being massaged, so as to synchronously explain the massage information and/or play a background music. For example, the sounding unit 7 can change the background music according to the massage information. In such case, since the projection unit 3 displays the massage information accompanied with an audible explanation, the user can be aware of massage information such as massage location, massage strength and massage manipulation more clearly. In addition, the background music can play a role of releasing pressure, and hence can relax the person being massaged; furthermore, since the background music can be changed at any time, it can prevent the person being massaged from being boring due to listening to the same music for a long time.

In the above-mentioned embodiments, the image recognition unit 2 can further be configured to, for example, obtain the image of the person being massaged at predetermined time interval and compare the massage information as determined with the image of the person being massaged; if the massage information is not matched with the image of the person being massaged, it sends warning information to the projection unit 3 and the sounding unit 7, respectively, to allow the projection unit 3 to display an alert and allow the sounding unit 7 to produce an alert sound.

It should be explained that, first of all, the predetermined time interval can be manually set or can be a time interval of moving from one massage location to another massage location; secondly, the image of the person being massaged can comprise an image presenting a full body of the person being massaged or can comprise an image presenting only a portion of the body contacted with the massager. Displaying the alert through the projection unit 3 or producing the alert sound through the sounding unit 6 can avoid faulty operation of the massager, thereby avoiding any injury of the person being massaged.

In the above-mentioned embodiments, as illustrated in FIG. 4, the main body 4 can be further provided with, for example, a physiotherapy unit 8 connected to the image recognition unit 2; in such case, the image recognition unit 2 is further configured to determine physiotherapy information based on the image of the person being massaged, wherein the physiotherapy information comprises physiotherapy location and physiotherapy power; the physiotherapy unit 8 is configured to emit light with certain wavelength according to the physiotherapy information as determined by the image recognition unit 2, so as to irradiate the physiotherapy location at the physiotherapy power. For example, the light with certain wavelength can have a wavelength between infrared light and ultraviolet light, or can be light applicable for phototherapy such as visible light or coherent light; furthermore, the physiotherapy unit can irradiate the physiotherapy location with light having only one wavelength or irradiate the physiotherapy location with light having multiple wavelengths; during irradiation, it requires to control a physiotherapy frequency to ensure that the total physiotherapy power is within a healthy physiotherapy range. With the setting of the physiotherapy unit 8, it can further improve the massage effect brought by the massage guiding device.

Figure 5:
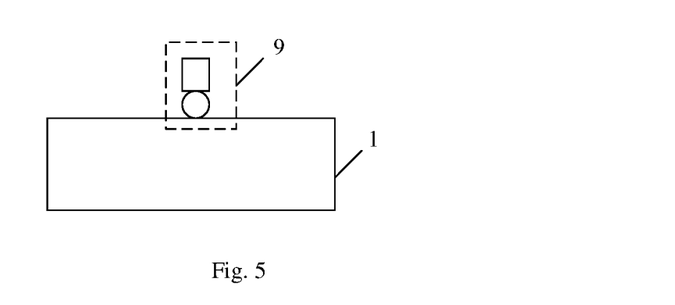
FIG. 5 is a schematic diagram illustrating a relationship between a mounting unit and a main body of a massage guiding device as provided by an embodiment of the present invention.

In the above-mentioned embodiments, the main body 1 can be further provided with a mounting unit 9; for example, as illustrated in FIG. 5, the mounting unit 9 is configured to mount the main body 1 at a ceiling by hanging it there or to mount the main body 1 on a supporting unit on a floor. It should be explained that, the location of the main body 1 can be arranged according to the location of the person being massaged, so as to prevent from blocking the visible light as emitted from the projection unit 3 during massage. Moreover, the connection between the mounting unit 9 and the main body 4 can be fixed or rotatable; and the rotational direction of the main body 1 can be adjusted according to the location of the massage. Neither a shape nor a structure of the mounting unit 9 is particularly defined in embodiments of the present invention and it only has to fix the main body 1 in a manner as described above.

Figure 6:
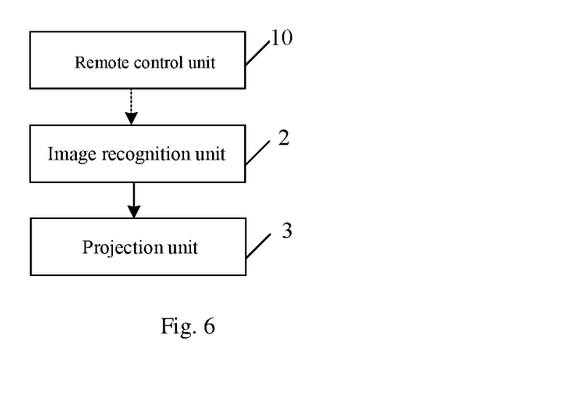
FIG. 6 is still another schematic diagram illustrating a massage guiding device as provided by an embodiment of the present invention.

In the above-mentioned embodiments, as illustrated in FIG. 6, for example, in order for the convenience of the user to set the basic information of the person being massaged, the massage guiding device can further comprise a remote control unit 10 connected to the image recognition unit 2, and the remote control unit 10 is configured to detect the basic information of the person being massaged as input by the user; in such case, the image recognition unit 2 is further configured to obtain the basic information as detected by the remote control unit 10 by means of wireless communication and to determine the massage information based on the image and the basic information of the person being massaged. It should be explained that, first of all, the remote control unit 10 can comprise a touch unit or a key unit to detect the basic information as input by the user; secondly, for the basic information of the person being massaged, reference can be made to the forgoing related description without repeating herein; thirdly, the wireless communication can be radio wave communication, or can be infrared communication or radio frequency communication or the like; fourthly, as illustrated in FIG. 5, the above-mentioned storage unit 4 can also store the basic information of the person being massaged as detected by the remote control unit 10. The remote control unit 10 is remotely connected to the image recognition unit 2 so that the user can modify the basic information through the remote control unit 10 while performing massage for convenience.

In the above-mentioned embodiments, as illustrated in FIG. 4, for example, the massage guiding device can further comprise a wearable unit 11 connected to the image recognition unit 2 in a wireless manner or wired manner; the wearable unit 11 is configured to detect a physiological parameter characteristic of the person being massaged; in such case, the image recognition unit 2 is further configured to obtain the physiological parameter characteristic as detected by the wearable unit 11, and determine the massage information based on the image and the physiological parameter characteristic of the person being massaged. It should be explained that, first of all, the wearable unit 11 can be any device which can be worn on the person being massaged such as bracelet, watch, shoes, cloth; secondly, the wearable unit 11 can be communicated with the image recognition unit 2 by means of wired communication or wireless communication; thirdly, the physiological parameter characteristic of the person being massaged can comprise blood pressure, heart rate, pulse, body temperature and the like; by way of example, when the body temperature of the person being massaged is raised, the image recognition unit 2 determines that the massage strength in the massage information is decreased, so as to lower the body temperature of the person being massaged; fourthly, the wearable unit 11 can further be combined with the image recognition unit 2 and the physiotherapy unit 8 so as to change the physiotherapy location and the physiotherapy power by detecting the physiological parameter characteristic of the person being massaged. By combining the physiological parameter characteristic as detected by the wearable unit 11 with the image of the person being massaged as obtained by the image recognition unit 2, the massage information can be optimized.

In the above-mentioned embodiments, in order for a person being massaged to be massaged by two users at the same time, the massage guiding device can comprise at least two projection units 3 which are connected to the image recognition unit 2 respectively; the respective projection units 3 emit visible light respectively according to the massage information as determined by the image recognition unit 2, so as to display the massage information on different portions of the body of the person being massaged. Since the at least two projection units 3 can display the massage information on different portions of the person being massaged, it allows two users to massage the same person being massaged simultaneously, so as to improve the massage efficiency.

In the above-mentioned embodiments, when several local massage operations are performed at the same time, for example, when a head massage and a foot massage are performed at the same time, the projection unit 3 may be blocked; thus in order for the local massage operations to be performed in parallel, the massage guiding device can comprise an image recognition unit 2 connected to the at least two projection units 3 respectively, so as to respectively recognize the image of the person being massaged and to respectively determine the massage information of the person being massaged, so as to allow the projection unit 3 connected thereto to project the massage information.

The Second Embodiment

Figure 7:
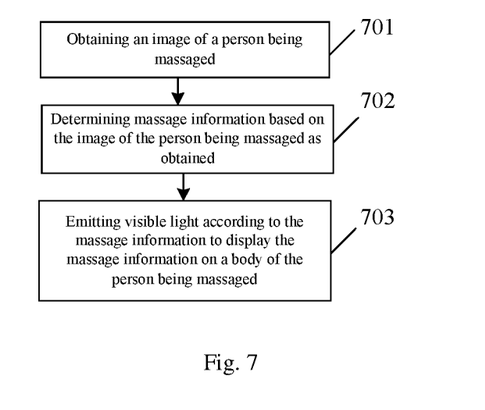
FIG. 7 is a flow chart illustrating a massage guiding method as provided by an embodiment of the present invention.

As illustrated in FIG. 7, embodiments of the present invention further provide a massage guiding method comprising steps S701-703 as below.

Step S701, obtaining an image of a person being massaged. By way of example, an image recognition unit obtains an image of a person being massaged by photography technology or scanning technology.

Step S702, determining massage information based on the image of the person being massaged as obtained. By way of example, the image recognition unit determines the massage information based on the image of the person being massaged as obtained.

Step S703, emitting visible light according to the massage information so as to display the massage information on a body of the person being massaged. By way of example, a projection unit emits visible light according to the massage information to display the massage information on the body of the person being massaged.

With the massage guiding method as provided by embodiments of the present invention, it can determine massage information based on the image of the person being massaged as obtained and then display the massage information on the body of the person being massaged; consequently, as compared with existing technology in which the massage information is not correct enough, embodiments of the present invention allow to accurately massage the person being massaged according to the massage information displayed on the body of the person being massaged without occurrence of incorrect massage location or improper massage strength, so as to achieve desired massage effect. Moreover, the massage is performed by following the massage information, thus it can avoid any injury to the body of the person being massaged.

In the above-mentioned embodiments, for example, before determining the massage information based on the image of the person being massaged, the method can further comprise detecting basic information of the person being massaged as input by a user; by way of example, the basic information as input can be detected by a setting unit. In such case, the step S702 can further comprise determining the massage information based on the image of the person being massaged as obtained and the basic information of the person being massaged as detected. By way of example, the image recognition unit determines the massage information based on the image of the person being massaged as obtained by the image recognition unit and the basic information of the person being massaged as detected by the setting unit. Since the massage information is further determined according to the basic information of the person being massaged, it can satisfy the demands from different people being massaged.

In the above-mentioned embodiments, for example, before determining the massage information based on the image of the person being massaged, the method can further comprise detecting the basic information of the person being massaged as input by the user and storing the basic information; by way of example, inputting the basic information of the person being massaged through the setting unit, and storing the basic information through a storage unit. In such case, the step S702 can further comprise determining the massage information based on the image of the person being massaged as obtained and the basic information of the person being massaged as stored. By way of example, the image recognition unit determines the massage information based on the image of the person being massaged as obtained by the image recognition unit and the basic information of the person being massaged as stored by the storage unit. It's no longer necessary for the user to repeatedly input the basic information of the person being massaged, because the massage information can be determined based on the basic information of the person being massaged as stored.

In the above-mentioned embodiments, for example, at the same time when emitting visible light to display the massage information on the body of the person being massaged, the method can further comprise producing a sound according to the massage information so as to explain the massage information and/or provide background music. By way of example, at the same time when the projection unit displays the massage information on the body of the person being massaged, a sounding unit produces a sound according to the massage information so as to explain the massage information and/or provide background music. Since the display of the massage information is accompanied with audio explanation, the user can be aware of massage information such as massage location, massage strength and massage manipulation more clearly. In addition, the background music can play a role of relaxing, so as to release the pressure of the person being massaged; moreover, the background music can be changed to prevent the person being massaged from being boring for listening to the same music for a long time.

In the above-mentioned embodiments, for example, after obtaining the image of the person being massaged, the method can further comprise: determining physiotherapy information based on the image of the person being massaged, wherein the physiotherapy information comprises physiotherapy location and physiotherapy power; and emitting light with certain wavelength according to the physiotherapy information, so as to irradiate the physiotherapy location at the physiotherapy power. By way of example, the image recognition unit determines the physiotherapy information based on the image of the person being massaged, wherein the physiotherapy information comprises physiotherapy location and physiotherapy power; and a physiotherapy unit then emits light with at least one wavelength in a range between infrared light and ultraviolet light, so as to irradiate the physiotherapy location at the physiotherapy power. By irradiating the person being massaged with physiotherapy light beams, it can further improve the health of the person being massaged.

In the above-mentioned embodiments, for example, before determining the massage information based on the image of the person being massaged, the method can further comprise detecting a physiological parameter characteristic of the person being massaged. By way of example, the physiological parameter characteristic of the person being massaged can be detected through a wearable unit. In such case, the step S702 can further comprise determining massage information based on the image and the physiological parameter characteristic of the person being massaged as obtained. By way of example, the image recognition unit determines the massage information based on the image and the physiological parameter characteristic of the person being massaged. By combining the physiological parameter characteristic of the person being massaged with the image of the person being massaged, it can optimize the massage information and further release the pressure of the person being massaged.

In an example, the step S703 can comprise emitting at least two beams of visible light according to the massage information so as to display the massage information on different portions of the body of the person being massaged. Since the at least two beams of visible light can display the massage information on different portions of the body of the person being massaged, it allows at least two users to massage the person being massaged simultaneously, so as to improve the massage efficiency.

In another example, the step S703 can further comprise displaying the massage information on the body of the person being massaged by rotating the visible light and changing a luminous flux of the visible light, so as to accommodate the body of the person being massaged. By way of example, a control unit rotates the visible light by controlling a rotation of a light output of the projection unit, so as to change the massage location displayed on the body of the person being massaged; and the control unit changes the luminous flux of the visible light by controlling a f-number of the light output of the projection unit, so as to clearly display the massage information on the body of the person being massaged.

Hereafter the above-mentioned steps will be further described in more details with two examples.

Figure 8:
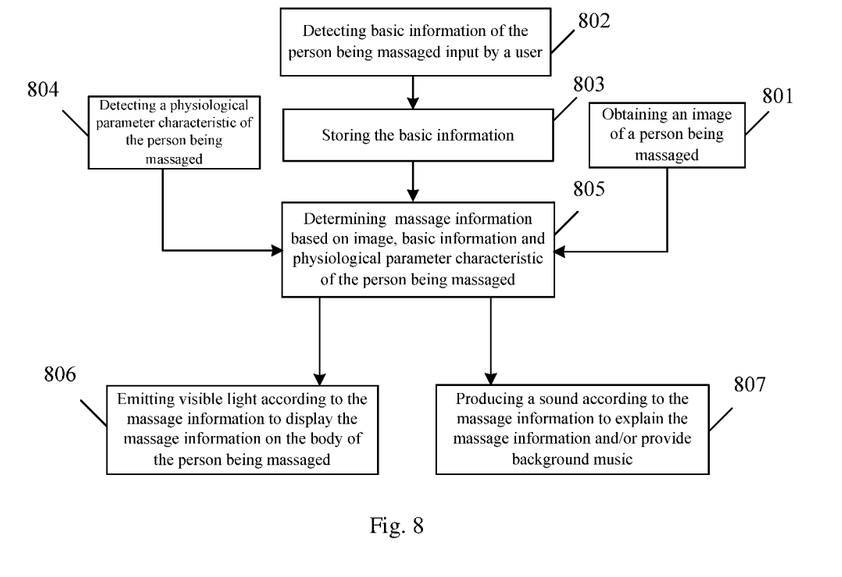
FIG. 8 is another flow chart illustrating a massage guiding method as provided by an embodiment of the present invention.

As illustrated in FIG. 8, one example of the massage guiding method as provided by embodiments of the present invention comprises steps as below.

Step S801, obtaining an image of a person being massaged; by way of example, obtaining the image of the person being massaged by an image recognition unit;

Step S802, detecting basic information of the person being massaged as input by a user; by way of example, detecting the basic information of the person being massaged as input by the user through a setting unit;

Step S803, storing the basic information; by way of example, storing the basic information as detected by the setting unit through a storage unit;

Step S804, detecting a physiological parameter characteristic of the person being massaged; by way of example, detecting the physiological parameter characteristic of the person being massaged by a wearable unit;

Step S805, determining the massage information based on the image, the basic information and the physiological parameter characteristic of the person being massaged; by way of example, determining the massage information by the image recognition unit based on the image, the basic information and the physiological parameter characteristic of the person being massaged;

Step S806, emitting visible light according to the massage information so as to display the massage information on the body of the person being massaged; by way of example, emitting the visible light by a projection unit so as to display the massage information on the body of the person being massaged;

Step S807, producing a sound according to the massage information so as to explain the massage information and/or provide background music; by way of example, producing a sound according to the massage information by a sounding unit so as to explain the massage information.

It should be explained that, a sequence of performing the above-mentioned steps S801, S802 and S804 is not particularly defined herein; in some examples, the step S806 and step S807 can be performed simultaneously.

Figure 9:
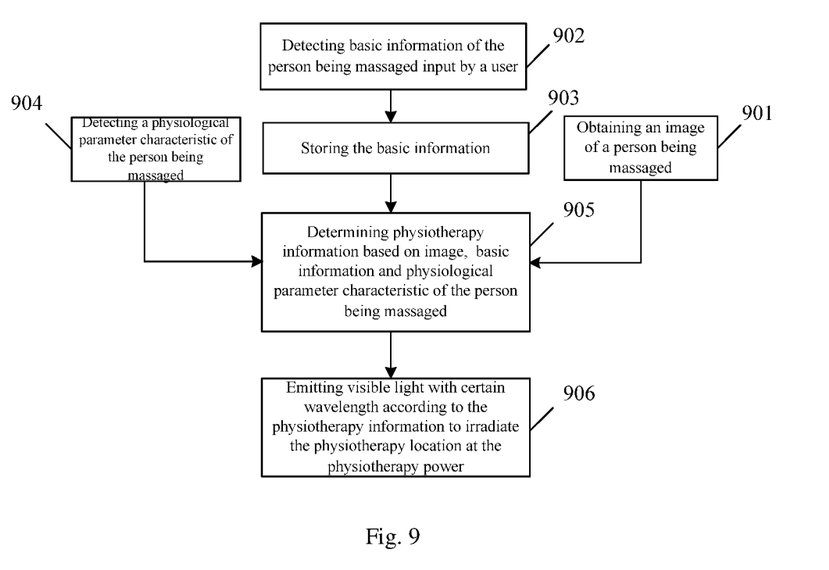
FIG. 9 is yet another flow chart illustrating a massage guiding method as provided by an embodiment of the present invention.

As illustrated in FIG. 9, another example of the massage guiding method as provided by embodiments of the present invention comprises steps as below.

Step S901, obtaining an image of a person being massaged; by way of example, obtaining the image of the person being massaged by an image recognition unit;

Step S902, detecting basic information of the person being massaged as input by a user; by way of example, detecting the basic information of the person being massaged as input by the user through a setting unit;

Step S903, storing the basic information of the person being massaged; by way of example, storing the basic information of the person being massaged as detected by the setting unit through a storage unit;

Step S904, detecting a physiological parameter characteristic of the person being massaged; by way of example, detecting the physiological parameter characteristic of the person being massaged by a wearable unit;

Step S905, determining physiotherapy information based on the image, the basic information and the physiological parameter characteristic of the person being massaged; by way of example, determining the physiotherapy information based on the image, the basic information and the physiological parameter characteristic of the person being massaged through the image recognition unit, wherein the physiotherapy information comprises physiotherapy location and physiotherapy power;

Step S906, emitting visible light with certain wavelength according to the physiotherapy information so as to irradiate the physiotherapy location at the physiotherapy power; by way of example, emitting light with at least one wavelength within a range from infrared light to ultraviolet light so as to irradiate the physiotherapy location at the physiotherapy power.

It should be explained that, a sequence of performing the above-mentioned steps S901, S902 and S904 is not particularly defined herein.

Embodiments in the description of the present invention are all described progressively with identical and similar portions thereof being referring to one another, each focusing on different contents over others. Especially, method embodiments are substantially similar with corresponding product embodiments and hence described in a simplified manner with relevant portions thereof referring to the description of the product embodiments.

It should be explained that the above-mentioned system embodiments are merely illustrated by way of example, in which units described as separate components may or may not be physically separated, and components illustrated as a single unit may or may not be a physical unit, that is, they can be located at a same place or can be distributed over a plurality of networked units. Objectives of the technical solution of embodiments of the present invention can be achieved by selecting part of or all modules thereof according to actual demands. Those skilled in the art can understand and also implement these embodiments without paying any creative works.

The foregoing embodiments are merely used for explaining the technical solution of the present invention, and not intended to limit the present invention; although the present invention is explained in detail with reference to the foregoing embodiments, those of ordinary skill in the art will readily appreciate that many modifications are possible in the foregoing embodiments, or equivalent substitutions are made for part of technical features; however, these modifications or substitutions are not intended to make the essences of the corresponding technical solutions depart from the spirit and the scope of the technical solutions of the embodiments of the present invention.

The present application claims priority of Chinese Patent Application No. 201510295787.3 filed on Jun. 2, 2015 titled "A MASSAGE GUIDING DEVICE AND A MASSAGE GUIDING METHOD", the disclosure of which is incorporated herein by reference in its entirety as part of the present application.

What is claimed is:

1. A massage guiding method, comprising:
obtaining an image of a person being massaged;
determining massage information based on the image of the person being massaged as obtained, massage information comprising at least one of massage location, massage sequence, massage direction, massage strength, massage duration and massage manipulation; and
emitting visible light according to the massage information as determined so as to display the massage information on a body of the person being massaged by at least one of:
displaying the massage sequence by moving a light spot in saltatory motion;
displaying the massage direction by moving a light spot in continuous motion;
displaying the massage strength by allowing a number of light circle around a light spot being in direct proportion to the massage strength;
displaying the massage duration by means of numbers or displaying the massage duration by moving a light spot to a next massage location upon a current massage duration is ended; and
displaying the massage manipulation by displaying signs on the body of the person being massaged.

2. The massage guiding method of claim 1, wherein before determining massage information based on the image of the person being massaged as obtained, the method further comprises detecting basic information of the person being massaged as input by a user; and
determining massage information based on the image of the person being massaged as obtained further comprises determining the massage information based on the image of the person being massaged and the basic information of the person being massaged as detected, wherein
the image of the person being massaged comprises posture information of the person being massaged, and the posture information of the person being massaged comprises one of sitting posture, lying posture and standing posture, wherein the lying posture comprises lying prostrate, lying supine and lying on side.

3. The massage guiding method of claim 1, wherein before determining massage information based on the image of the person being massaged as obtained, the method further comprises: detecting basic information of the person being massaged as input by a user; and storing the basic information; wherein,
determining massage information based on the image of the person being massaged as obtained further comprises determining the massage information based on the image of the person being massaged as obtained and the basic information as stored, wherein the image of the person being massaged comprises posture information of the person being massaged, and the posture information of the person being massaged comprises one of sitting posture, lying posture and standing posture, wherein the lying posture comprises lying prostrate, lying supine and lying on side.

4. The massage guiding method of claim 1, wherein while emitting visible light according to the massage information as determined so as to display the massage information on the body of the person being massaged, the method further comprises:
producing a sound according to the massage information as determined so as to perform at least one of explaining the massage information and providing background music.

5. The massage guiding method of claim 1, wherein after obtaining the image of the person being massaged, the method further comprises:
determining physiotherapy information based on the image of the person being massaged as obtained, wherein the physiotherapy information comprises physiotherapy location and physiotherapy power; and
emitting light with a certain wavelength according to the physiotherapy information so as to irradiate the physiotherapy location at the physiotherapy power.

6. The massage guiding method of claim 1, wherein before determining massage information based on the image of the person being massaged as obtained, the method further comprises detecting a physiological parameter characteristic of the person being massaged; and
determining massage information based on the image of the person being massaged as obtained further comprises determining the massage information based on the image of the person being massaged as obtained and the physiological parameter characteristic, wherein
the physiological parameter characteristic of the person being massaged comprises blood pressure, heart rate, pulse, body temperature.

7. The massage guiding method of claim 1, wherein emitting visible light according to the massage information as determined so as to display the massage information on the body of the person being massaged comprises:
emitting at least two beams of visible light according to the massage information as determined so as to display the massage information on different portions of the body of the person being massaged simultaneously.

8. The massage guiding method of claim 1, wherein emitting visible light according to the massage information as determined so as to display the massage information on a body of the person being massaged further comprises:
adapting to the body of the person being massaged by at least one of rotating the visible light and changing an illumination flux of the visible light so as to display corresponding massage information.

* * * * *